10

(12) United States Patent
Wang et al.

(10) Patent No.: US 8,192,965 B2
(45) Date of Patent: Jun. 5, 2012

(54) PRODUCING ITACONIC ACID IN YEAST USING GLYCEROL AS THE SUBSTRATE

(75) Inventors: Jia-Hung Wang, Taichung County (TW); Shu-Hsien Tsai, Kaohsiung (TW); Kelly Teng, San Diego, CA (US)

(73) Assignee: Industrial Technology Research Institute, Hsinchu (TW)

( * ) Notice: Subject to any disclaimer, the term of this patent is extended or adjusted under 35 U.S.C. 154(b) by 185 days.

(21) Appl. No.: 12/546,834

(22) Filed: Aug. 25, 2009

(65) Prior Publication Data

US 2011/0053232 A1  Mar. 3, 2011

(51) Int. Cl.
*C12P 7/44* (2006.01)
*C12P 7/46* (2006.01)
*C12P 21/06* (2006.01)
*C12N 1/00* (2006.01)
*C12N 15/70* (2006.01)
*C07H 21/06* (2006.01)

(52) U.S. Cl. .... 435/142; 435/145; 435/69.1; 435/254.2; 435/254.22; 435/320.1; 536/23.2

(58) Field of Classification Search .................. None
See application file for complete search history.

(56) References Cited

U.S. PATENT DOCUMENTS 7,479,381 B1    1/2009  Kuo et al.
2010/0285546 A1 *  11/2010  Liao et al. ............... 435/145

FOREIGN PATENT DOCUMENTS

| EP | 2 017 344 | 1/2009 |
| JP | 2008-182936 | 8/2008 |
| JP | 2009-027999 | 2/2009 |
| WO | WO 2009/014437 | 1/2009 |

OTHER PUBLICATIONS

Kanamasa et al. Biotechnol and Bioprocess Engineering 2007, 12: 92-99.*
Shin Kanamasa et al., "Cloning and Functional Characterization of the *cis*-aconitic acid decarboxylase (CAD) gene from *Aspergillus terreus*"; Applied Microbiology and Biotechnology, vol. 80, No. 2, pp. 223-229 (2008).

* cited by examiner

*Primary Examiner* — Robert Mondesi
*Assistant Examiner* — Iqbal H Chowdhury
(74) *Attorney, Agent, or Firm* — Occhiuti Rohlicek & Tsao LLP

(57) ABSTRACT

Method for producing itaconic acid in yeast cells using glycerol as the substrate. The yeast cells express cis-aconitic acid decarboxylase and optionally, citrate synthase and/or aconitase at high levels.

7 Claims, 4 Drawing Sheets

SEQUENCE LISTING

```
<160> NUMBER OF SEQ ID NOS: 10

<210> SEQ ID NO 1
<211> LENGTH: 38
<212> TYPE: PRT
<213> ORGANISM: Artificial Sequence
<220> FEATURE:
<223> OTHER INFORMATION: Leader Sequence

<400> SEQUENCE: 1

Met Ser Ala Ile Leu Ser Thr Thr Ser Lys Ser Phe Leu Ser Arg Gly
1               5                   10                  15

Ser Thr Arg Gln Cys Gln Asn Met Gln Lys Ala Leu Phe Ala Leu Leu
            20                  25                  30

Asn Ala Arg His Tyr Ser
        35

<210> SEQ ID NO 2
<211> LENGTH: 15
<212> TYPE: PRT
<213> ORGANISM: Artificial Sequence
<220> FEATURE:
```

<223> OTHER INFORMATION: Leader Sequence

<400> SEQUENCE: 2

Met Lys Leu Ala Thr Ala Phe Thr Ile Leu Thr Ala Val Leu Ala
1               5                   10                  15

<210> SEQ ID NO 3
<211> LENGTH: 1473
<212> TYPE: DNA
<213> ORGANISM: Aspergillus terreus

<400> SEQUENCE: 3

```
atgaccaagc agtctgctga ttccaacgcg aagtctggtg tgacctctga gatctgtcac      60
tgggcgtcta atctcgccac tgatgatatc ccgagcgacg ttctggagcg tgcaaaatac     120
ctgatcctgg atggtatcgc gtgcgcgtgg gtaggtgctc gtgtcccatg gtctgaaaaa     180
tacgttcaag cgaccatgtc tttcgaacct ccgggtgcgt gtcgtgtcat cggttacggc     240
cagaaactgg gtccggtagc ggctgccatg acgaactctg catttattca ggcgaccgaa     300
ctcgatgact atcactctga agcgccgctg cattccgcgt ctatcgttct cccggcagtt     360
ttcgcggcga gcgaagtact ggccgaacag gtaaaaacca tctctggtat tgacgtgatt     420
ctggctgcga tcgttggttt cgagagcggt cctcgcatcg gcaaagcgat ctacggttct     480
gacctcctga caacggctg gcactgcggt gcggtatatg gcgcaccggc tggtgcgctc     540
gcaactggta agctcctggg cctcacgccg acagcatgg aagatgcact gggtattgcc     600
tgcacgcaag catgcggcct catgtccgcg cagtatggtg gcatggttaa acgtgttcag     660
cacggtttcg cagcgcgtaa tggtctcctc ggtggcctcc tggctcacgg cggctacgag     720
gcgatgaaag tgttctcga cgttcttac ggtggcttcc tgaagatgtt caccaagggc     780
aacggtcgtg aaccgccgta caagaagaa gaggttgtgg ctggtctggg tagcttctgg     840
cacaccttca ccattcgtat caaactgtac gcgtgctgcg gtctcgtaca cggtcctgtt     900
gaagccattg aaaacctcca gggtcgttac ccggaactgc tcaatcgtgc taacctgtct     960
aacatccgcc acgttcacgt acaactctct accgcgagca actcccactg tggttggatc    1020
ccagaagagc gcccaatctc ttctatcgcg ggtcaaatgt ctgtcgcata tcctcgcc      1080
gttcagctcg ttgaccaaca gtgtctgctc agccagttct ccgagtttga cgataatctg    1140
gaacgcccgg aagtgtggga cctggcacgt aaggttacca gctctcaatc tgaggagttc    1200
gaccaggacg gtaactgtct ctctgccggt cgcgtccgta ttgagttcaa cgacggctcc    1260
tccatcaccg aatccgttga agccgctc ggtgtaaagg aaccaatgcc aaatgaacgc     1320
atcctgcaca ataccgtac cctggcgggt tctgtaacgg acgaaagccg tgttaaggag    1380
atcgaggatc tcgtgctcgg cctggaccgt ctgaccgata ttagcccgct cctcgagctg    1440
ctgaattgtc cggttaaatc cccactggtt taa                                 1473
```

<210> SEQ ID NO 4
<211> LENGTH: 490
<212> TYPE: PRT
<213> ORGANISM: Aspergillus terreus

<400> SEQUENCE: 4

Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
                20                  25                  30

Asp Val Leu Glu Arg Ala Lys Tyr Leu Ile Leu Asp Gly Ile Ala Cys

```
                35                  40                  45
Ala Trp Val Gly Ala Arg Val Pro Trp Ser Glu Lys Tyr Val Gln Ala
 50                  55                  60

Thr Met Ser Phe Glu Pro Pro Gly Ala Cys Arg Val Ile Gly Tyr Gly
 65                  70                  75                  80

Gln Lys Leu Gly Pro Val Ala Ala Met Thr Asn Ser Ala Phe Ile
                 85                  90                  95

Gln Ala Thr Glu Leu Asp Asp Tyr His Ser Glu Ala Pro Leu His Ser
                100                 105                 110

Ala Ser Ile Val Leu Pro Ala Val Phe Ala Ala Ser Glu Val Leu Ala
                115                 120                 125

Glu Gln Gly Lys Thr Ile Ser Gly Ile Asp Val Ile Leu Ala Ala Ile
130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
                180                 185                 190

Met Glu Asp Ala Leu Gly Ile Ala Cys Thr Gln Ala Cys Gly Leu Met
                195                 200                 205

Ser Ala Gln Tyr Gly Gly Met Val Lys Arg Val Gln His Gly Phe Ala
                210                 215                 220

Ala Arg Asn Gly Leu Leu Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Val
                260                 265                 270

Val Ala Gly Leu Gly Ser Phe Trp His Thr Phe Thr Ile Arg Ile Lys
                275                 280                 285

Leu Tyr Ala Cys Cys Gly Leu Val His Gly Pro Val Glu Ala Ile Glu
290                 295                 300

Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
                325                 330                 335

Cys Gly Trp Ile Pro Glu Glu Arg Pro Ile Ser Ser Ile Ala Gly Gln
                340                 345                 350

Met Ser Val Ala Tyr Ile Leu Ala Val Gln Leu Val Asp Gln Gln Cys
                355                 360                 365

Leu Leu Ser Gln Phe Ser Glu Phe Asp Asp Asn Leu Glu Arg Pro Glu
                370                 375                 380

Val Trp Asp Leu Ala Arg Lys Val Thr Ser Ser Gln Ser Glu Glu Phe
385                 390                 395                 400

Asp Gln Asp Gly Asn Cys Leu Ser Ala Gly Arg Val Arg Ile Glu Phe
                405                 410                 415

Asn Asp Gly Ser Ser Ile Thr Glu Ser Val Glu Lys Pro Leu Gly Val
                420                 425                 430

Lys Glu Pro Met Pro Asn Glu Arg Ile Leu His Lys Tyr Arg Thr Leu
                435                 440                 445

Ala Gly Ser Val Thr Asp Glu Ser Arg Val Lys Glu Ile Glu Asp Leu
450                 455                 460
```

Val Leu Gly Leu Asp Arg Leu Thr Asp Ile Ser Pro Leu Leu Glu Leu
465                 470                 475                 480

Leu Asn Cys Pro Val Lys Ser Pro Leu Val
                485                 490

<210> SEQ ID NO 5
<211> LENGTH: 1284
<212> TYPE: DNA
<213> ORGANISM: Escherichia coli

<400> SEQUENCE: 5
atggctgata caaaagcaaa actcacccte aacggggata cagctgttga actggatgtg      60
ctgaaaggca cgctgggtca gatgttatt gatatccgta ctctcggttc aaaaggtgtg     120
ttcacctttg acccaggctt cacttcaacc gcatcctgcg aatctaaaat tactttatt    180 gatggtgatg aaggtatttt gctgcaccgc ggtttcccga tcgatcagct ggcgaccgat     240
tctaactacc tggaagtttg ttacatcctg ctgaatggtg aaaaaccgac tcaggaacag     300
tatgacgaat ttaaaactac ggtgacccgt cataccatga tccacgagca gattacccgt     360
ctgttccatg ctttccgtcg cgactcgcat ccaatggcag tcatgtgtgg tattaccggc     420
gcgctggcgg cgttctatca cgactcgctg gatgttaaca atcctcgtca ccgtgaaatt     480
gccgcgttcc gcctgctgtc gaaaatgccg accatggccg cgatgtgtta caagtattcc     540
attggtcagc catttgttta cccgcgcaac gatctctcct acgccggtaa cttcctgaat     600
atgatgttct ccacgccgtg cgaaccgtat gaagttaatc cgattctgga acgtgctatg     660
gaccgtattc tgatcctgca cgctgaccat gaacagaacg cctctacctc caccgtgcgt     720
accgctggct cttcgggtgc gaacccgttt gcctgtatcg cagcaggtat tgcttcactg     780
tggggacctg cgcacggcgg tgctaacgaa gcggcgctga aatgctgga agaaatcagc     840 tccgttaaac acattccgga atttgttcgt cgtgcgaaag acaaaaatga ttctttccgc     900
ctgatgggct tcggtcaccg cgtgtacaaa aattacgacc cgcgcgccac cgtaatgcgt     960
gaaacctgcc atgaagtgct gaaagagctg ggcacgaagg atgacctgct ggaagtggct    1020
atggagctgg aaaacatcgc gctgaacgac ccgtacttta tcgagaagaa actgtacccg    1080
aacgtcgatt tctactctgg tatcatcctg aaagcgatgg gtattccgtc ttccatgttc    1140
accgtcattt tcgcaatggc acgtaccgtt ggctggatcg cccactggag cgaaatgcac    1200
agtgacggta tgaagattgc ccgtccgcgt cagctgtata caggatatga aaaacgcgac    1260
tttaaaagcg atatcaagcg ttaa                                          1284

<210> SEQ ID NO 6
<211> LENGTH: 427
<212> TYPE: PRT
<213> ORGANISM: Escherichia coli

<400> SEQUENCE: 6

Met Ala Asp Thr Lys Ala Lys Leu Thr Leu Asn Gly Asp Thr Ala Val
1               5                   10                  15

Glu Leu Asp Val Leu Lys Gly Thr Leu Gly Gln Asp Val Ile Asp Ile
                20                  25                  30

Arg Thr Leu Gly Ser Lys Gly Val Phe Thr Phe Asp Pro Gly Phe Thr
            35                  40                  45

Ser Thr Ala Ser Cys Glu Ser Lys Ile Thr Phe Ile Asp Gly Asp Glu
        50                  55                  60

Gly Ile Leu Leu His Arg Gly Phe Pro Ile Asp Gln Leu Ala Thr Asp
65                  70                  75                  80

Ser Asn Tyr Leu Glu Val Cys Tyr Ile Leu Leu Asn Gly Lys Pro
                85                  90                  95

Thr Gln Glu Gln Tyr Asp Glu Phe Lys Thr Val Thr Arg His Thr
            100                 105                 110

Met Ile His Glu Gln Ile Thr Arg Leu Phe His Ala Phe Arg Arg Asp
        115                 120                 125

Ser His Pro Met Ala Val Met Cys Gly Ile Thr Gly Ala Leu Ala Ala
    130                 135                 140

Phe Tyr His Asp Ser Leu Asp Val Asn Asn Pro Arg His Arg Glu Ile
145                 150                 155                 160

Ala Ala Phe Arg Leu Leu Ser Lys Met Pro Thr Met Ala Ala Met Cys
                165                 170                 175

Tyr Lys Tyr Ser Ile Gly Gln Pro Phe Val Tyr Pro Arg Asn Asp Leu
                180                 185                 190

Ser Tyr Ala Gly Asn Phe Leu Asn Met Met Phe Ser Thr Pro Cys Glu
                195                 200                 205

Pro Tyr Glu Val Asn Pro Ile Leu Glu Arg Ala Met Asp Arg Ile Leu
    210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
                245                 250                 255

Ile Ala Ser Leu Trp Gly Pro Ala His Gly Gly Ala Asn Glu Ala Ala
                260                 265                 270

Leu Lys Met Leu Glu Glu Ile Ser Ser Val Lys His Ile Pro Glu Phe
            275                 280                 285

Val Arg Arg Ala Lys Asp Lys Asn Asp Ser Phe Arg Leu Met Gly Phe
            290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
                325                 330                 335

Leu Glu Val Ala Met Glu Leu Glu Asn Ile Ala Leu Asn Asp Pro Tyr
            340                 345                 350

Phe Ile Glu Lys Lys Leu Tyr Pro Asn Val Asp Phe Tyr Ser Gly Ile
        355                 360                 365

Ile Leu Lys Ala Met Gly Ile Pro Ser Ser Met Phe Thr Val Ile Phe
    370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Thr Gly Tyr
                405                 410                 415

Glu Lys Arg Asp Phe Lys Ser Asp Ile Lys Arg
            420                 425

<210> SEQ ID NO 7
<211> LENGTH: 2676
<212> TYPE: DNA
<213> ORGANISM: Escherichia coli

<400> SEQUENCE: 7
atgtcgtcaa ccctacgaga agccagtaag gacacgttgc aggccaaaga taaaacttac      60
cactactaca gcctgccgct tgctgctaaa tcactgggcg atatcacccg tctacccaag     120
tcactcaaag ttttgctcga aaacctgctg cgctggcagg atggtaactc ggttaccgaa     180

```
gaggatatcc acgcgctggc aggatggctg aaaaatgccc atgctgaccg tgaaattgcc      240
taccgcccgg caagggtgct gatgcaggac tttaccggcg tacctgccgt tgttgatctg      300
gcggcaatgc gcgaagcggt taaacgcctc ggcggcgata ctgcaaaggt taacccgctc      360
tcaccggtcg acctggtcat tgaccactcg gtgaccgtcg atcgttttgg tgatgatgag      420
gcatttgaag aaaacgtacg cctggaaatg gagcgcaacc acgaacgtta tgtgttcctg      480
aaatggggaa agcaagcgtt cagtcggttt agcgtcgtgc cgccaggcac aggcatttgc      540
catcaggtta acctcgaata tctcggcaaa gcagtgtgga gtgaattgca ggacggtgaa      600
tggattgctt atccggatac actcgttggt actgactcgc acaccaccat gatcaacggc      660
cttggcgtgc tggggtgggg cgttggtggg atcgaagcag aagccgcaat gttaggccag      720
ccggtttcca tgcttatccc ggatgtagtg ggcttcaaac ttaccggaaa attacgtgaa      780
ggtattaccg ccacagacct ggttctcact gttacccaaa tgctgcgcaa acatggcgtg      840
gtggggaaat tcgtcgaatt ttatggtgat ggtctggatt cactaccgtt ggcggatcgc      900
gccaccattg ccaatatgtc gccagaatat ggtgccacct gtggcttctt cccaatcgat      960
gctgtaaccc tcgattacat gcgtttaagc gggcgcagcg aagatcaggt cgagttggtc     1020
gaaaaatatg ccaaagcgca gggcatgtgg cgtaacccgg gcgatgaacc aattttttacc    1080 agtacgttag aactggatat gaatgacgtt gaagcgagcc tggcagggcc taaacgccca     1140
caggatcgcg ttgcactgcc cgatgtacca aaagcatttg ccgccagtaa cgaactggaa     1200
gtgaatgcca cgcataaaga tcgccagccg gtcgattatg ttatgaacgg acatcagtat     1260
cagttacctg atggcgctgt ggtcattgct gcgataaacct cgtgcaccaa cacctctaac    1320
ccaagtgtgc tgatggccgc aggcttgctg gcgaaaaaag ccgtaactct gggcctcaag    1380
cggcaaccat gggtcaaagc gtcgctggca ccgggttcga aagtcgtttc tgattatctg     1440
gcaaaagcga aactgacacc gtatctcgac gaactggggt ttaaccttgt gggatacggt     1500
tgtaccacct gtattggtaa ctctgggccg ctgcccgatc ctatcgaaac ggcaatcaaa     1560
aaaagcgatt taaccgtcgg tgcggtgctg tccggcaacc gtaactttga aggccgtatc     1620
catccgctgg ttaaaactaa ctggctggcc tcgccgccgc tggtggttgc ctatgcgctg     1680
gcggaaaata tgaatatcaa cctggcttct gagcctatcg ccatgatcg caaaggcgat      1740 ccggtttatc tgaaagatat ctggccatcg gcacaagaaa ttgcccgtgc ggtagaacaa     1800
gtctccacag aaatgttccg caaagagtac gcagaagttt ttgaaggcac agcagagtgg     1860
aagggaatta acgtcacacg atccgatacc tacggttggc aggaggactc aacctatatt     1920
cgcttatcgc ctttctttga tgaaatgcag gcaacaccag caccagtgga agatattcac     1980
ggtgcgcgga tcctcgcaat gctgggggat tcagtcacca ctgaccatat ctctccggcg     2040
ggcagtatta agcccgacag cccagcgggt cgatatctac aaggtcgggg tgttgagcga     2100
aaagacttta actcctacgg ttcgcggcgt ggtaaccatg aagtgatgat gcgcggcacc     2160
ttcgccaata ttcgcatccg taatgaaatg gtgcctggcg ttgaaggggg gatgacgcgg     2220
catttacctg acagcgacgt agtctctatt tatgatgctg cgatgcgcta taagcaggag     2280
caaacgccgc tggcggtgat tgccgggaaa gagtatggat caggctccag tcgtgactgg     2340
gcggcaaaag gtccgcgtct gcttggtatt cgtgtggtga ttgccgaatc gtttgaacga     2400
attcaccgtt cgaatttaat tggcatgggc atcctgccgc tggaatttcc gcaaggcgta     2460
acgcgtaaaa cgttagggct aaccggggaa gagaagatta atattggcga tctgcaaaac    2520
ctacaacccg gcgcgacggt tccggtgacg cttacgcgcg cggatggtag ccaggaagtc     2580
```

-continued

```
gtaccctgcc gttgtcgtat cgacaccgcg acggagttga cctactacca gaacgacggc    2640
attttgcatt atgtcattcg taatatgttg aagtaa    2676
```

<210> SEQ ID NO 8
<211> LENGTH: 891
<212> TYPE: PRT
<213> ORGANISM: Escherichia coli

<400> SEQUENCE: 8

Met Ser Ser Thr Leu Arg Glu Ala Ser Lys Asp Thr Leu Gln Ala Lys
1               5                   10                  15

Asp Lys Thr Tyr His Tyr Tyr Ser Leu Pro Leu Ala Ala Lys Ser Leu
            20                  25                  30

Gly Asp Ile Thr Arg Leu Pro Lys Ser Leu Lys Val Leu Leu Glu Asn
        35                  40                  45

Leu Leu Arg Trp Gln Asp Gly Asn Ser Val Thr Glu Glu Asp Ile His
    50                  55                  60

Ala Leu Ala Gly Trp Leu Lys Asn Ala His Ala Asp Arg Glu Ile Ala
65                  70                  75                  80

Tyr Arg Pro Ala Arg Val Leu Met Gln Asp Phe Thr Gly Val Pro Ala
                85                  90                  95

Val Val Asp Leu Ala Ala Met Arg Glu Ala Val Lys Arg Leu Gly Gly
            100                 105                 110

Asp Thr Ala Lys Val Asn Pro Leu Ser Pro Val Asp Leu Val Ile Asp
        115                 120                 125

His Ser Val Thr Val Asp Arg Phe Gly Asp Asp Glu Ala Phe Glu Glu
    130                 135                 140

Asn Val Arg Leu Glu Met Glu Arg Asn His Glu Arg Tyr Val Phe Leu
145                 150                 155                 160

Lys Trp Gly Lys Gln Ala Phe Ser Arg Phe Ser Val Val Pro Pro Gly
                165                 170                 175

Thr Gly Ile Cys His Gln Val Asn Leu Glu Tyr Leu Gly Lys Ala Val
            180                 185                 190

Trp Ser Glu Leu Gln Asp Gly Glu Trp Ile Ala Tyr Pro Asp Thr Leu
        195                 200                 205

Val Gly Thr Asp Ser His Thr Thr Met Ile Asn Gly Leu Gly Val Leu
    210                 215                 220

Gly Trp Gly Val Gly Gly Ile Glu Ala Glu Ala Ala Met Leu Gly Gln
225                 230                 235                 240

Pro Val Ser Met Leu Ile Pro Asp Val Val Gly Phe Lys Leu Thr Gly
                245                 250                 255

Lys Leu Arg Glu Gly Ile Thr Ala Thr Asp Leu Val Leu Thr Val Thr
            260                 265                 270

Gln Met Leu Arg Lys His Gly Val Val Gly Lys Phe Val Glu Phe Tyr
        275                 280                 285

Gly Asp Gly Leu Asp Ser Leu Pro Leu Ala Asp Arg Ala Thr Ile Ala
    290                 295                 300

Asn Met Ser Pro Glu Tyr Gly Ala Thr Cys Gly Phe Phe Pro Ile Asp
305                 310                 315                 320

Ala Val Thr Leu Asp Tyr Met Arg Leu Ser Gly Arg Ser Glu Asp Gln
                325                 330                 335

Val Glu Leu Val Glu Lys Tyr Ala Lys Ala Gln Gly Met Trp Arg Asn
            340                 345                 350

Pro Gly Asp Glu Pro Ile Phe Thr Ser Thr Leu Glu Leu Asp Met Asn

```
                355                 360                 365
Asp Val Glu Ala Ser Leu Ala Gly Pro Lys Arg Pro Gln Asp Arg Val
370                 375                 380
Ala Leu Pro Asp Val Pro Lys Ala Phe Ala Ala Ser Asn Glu Leu Glu
385                 390                 395                 400
Val Asn Ala Thr His Lys Asp Arg Gln Pro Val Asp Tyr Val Met Asn
                405                 410                 415
Gly His Gln Tyr Gln Leu Pro Asp Gly Ala Val Ile Ala Ala Ile
            420                 425                 430
Thr Ser Cys Thr Asn Thr Ser Asn Pro Ser Val Leu Met Ala Ala Gly
        435                 440                 445
Leu Leu Ala Lys Lys Ala Val Thr Leu Gly Leu Lys Arg Gln Pro Trp
450                 455                 460
Val Lys Ala Ser Leu Ala Pro Gly Ser Lys Val Val Ser Asp Tyr Leu
465                 470                 475                 480
Ala Lys Ala Lys Leu Thr Pro Tyr Leu Asp Glu Leu Gly Phe Asn Leu
                485                 490                 495
Val Gly Tyr Gly Cys Thr Thr Cys Ile Gly Asn Ser Gly Pro Leu Pro
            500                 505                 510
Asp Pro Ile Glu Thr Ala Ile Lys Lys Ser Asp Leu Thr Val Gly Ala
        515                 520                 525
Val Leu Ser Gly Asn Arg Asn Phe Glu Gly Arg Ile His Pro Leu Val
530                 535                 540
Lys Thr Asn Trp Leu Ala Ser Pro Pro Leu Val Val Ala Tyr Ala Leu
545                 550                 555                 560
Ala Gly Asn Met Asn Ile Asn Leu Ala Ser Glu Pro Ile Gly His Asp
                565                 570                 575
Arg Lys Gly Asp Pro Val Tyr Leu Lys Asp Ile Trp Pro Ser Ala Gln
            580                 585                 590
Glu Ile Ala Arg Ala Val Glu Gln Val Ser Thr Glu Met Phe Arg Lys
        595                 600                 605
Glu Tyr Ala Glu Val Phe Glu Gly Thr Ala Glu Trp Lys Gly Ile Asn
610                 615                 620
Val Thr Arg Ser Asp Thr Tyr Gly Trp Gln Glu Asp Ser Thr Tyr Ile
625                 630                 635                 640
Arg Leu Ser Pro Phe Phe Asp Glu Met Gln Ala Thr Pro Ala Pro Val
                645                 650                 655
Glu Asp Ile His Gly Ala Arg Ile Leu Ala Met Leu Gly Asp Ser Val
            660                 665                 670
Thr Thr Asp His Ile Ser Pro Ala Gly Ser Ile Lys Pro Asp Ser Pro
        675                 680                 685
Ala Gly Arg Tyr Leu Gln Gly Arg Gly Val Glu Arg Lys Asp Phe Asn
690                 695                 700
Ser Tyr Gly Ser Arg Arg Gly Asn His Glu Val Met Met Arg Gly Thr
705                 710                 715                 720
Phe Ala Asn Ile Arg Ile Arg Asn Glu Met Val Pro Gly Val Glu Gly
                725                 730                 735
Gly Met Thr Arg His Leu Pro Asp Ser Asp Val Val Ser Ile Tyr Asp
            740                 745                 750
Ala Ala Met Arg Tyr Lys Gln Glu Gln Thr Pro Leu Ala Val Ile Ala
        755                 760                 765
Gly Lys Glu Tyr Gly Ser Gly Ser Ser Arg Asp Trp Ala Ala Lys Gly
770                 775                 780
```

```
Pro Arg Leu Leu Gly Ile Arg Val Val Ile Ala Glu Ser Phe Glu Arg
785                 790                 795                 800

Ile His Arg Ser Asn Leu Ile Gly Met Gly Ile Leu Pro Leu Glu Phe
            805                 810                 815

Pro Gln Gly Val Thr Arg Lys Thr Leu Gly Leu Thr Gly Glu Glu Lys
        820                 825                 830

Ile Asp Ile Gly Asp Leu Gln Asn Leu Gln Pro Gly Ala Thr Val Pro
    835                 840                 845

Val Thr Leu Thr Arg Ala Asp Gly Ser Gln Glu Val Val Pro Cys Arg
850                 855                 860

Cys Arg Ile Asp Thr Ala Thr Glu Leu Thr Tyr Tyr Gln Asn Asp Gly
865                 870                 875                 880

Ile Leu His Tyr Val Ile Arg Asn Met Leu Lys
            885                 890

<210> SEQ ID NO 9
<211> LENGTH: 2598
<212> TYPE: DNA
<213> ORGANISM: Escherichia coli

<400> SEQUENCE: 9
atgctagaag aataccgtaa gcacgtagct gagcgtgccg ctgaggggat tgcgcccaaa      60
cccctggatg caaaccaaat ggccgcactt gtagagctgc tgaaaaaccc gcccgcgggc     120
gaagaagaat tcctgttaga tctgttaacc aaccgtgttc ccccaggcgt cgatgaagcc     180
gcctatgtca aagcaggctt cctggctgct atcgcgaaag gcgaagccaa atcccctctg     240
ctgactccgg aaaaagccat cgaactgctg ggcaccatgc agggtggtta caacattcat     300
ccgctgatcg acgcgctgga tgatgccaaa ctggcaccta tgctgccaa agcactttct      360 cacacgctgc tgatgttcga taacttctat gacgtagaag agaaagcgaa agcaggcaac     420
gaatatgcga agcaggttat gcagtcctgg gcggatgccg aatggttcct gaatcgcccg     480
gcgctggctg aaaaactgac cgttactgtc ttcaaagtca ctggcgaaac taacaccgat     540
gaccttcctc cggcaccgga tgcgtggtca cgcccggata tcccactgca cgcgctggcg     600
atgctgaaaa acgcccgtga aggtattgag ccagaccagc ctggtgttgt tggtccgatc     660
aagcaaatcg aagctctgca acagaaaggt ttcccgctgg cgtacgtcgg tgacgttgtg     720
ggtacgggtt cttcgcgtaa atccgccact aactccgttc tgtggtttat gggcgatgat     780
attccacatg tgccgaacaa acgcggcggt ggtttgtgcc tcggcggtaa aattgcaccc     840
atcttcttta acacgatgga agacgcgggt gcactgccaa tcgaagtcga cgtctctaac     900
ctgaacatgg cgacgtgat tgacgtttac ccgtacaaag tgaagtgcg taaccacgaa      960 accggcgaac tgctggcgac cttcgaactg aaaaccgacg tgctgattga tgaagtgcgt    1020
gctggtggcc gtattccgct gattatcggg cgtggcctga ccaccaaagc gcgtgaagca    1080
cttggtctgc cgcacagtga tgtgttccgt caggcgaaag atgtcgctga gagcgatcgc    1140
ggcttctcgc tggcgcaaaa aatggtaggc cgtgcctgtg cgtgaaagg cattcgtccg    1200 ggcgcgtact gtgaaccgaa aatgacttct gtaggttccc aggacaccac cggcccgatg    1260
acccgtgatg aactgaaaga cctgcgtgc ctgggcttct cggctgacct ggtgatgcag     1320
tctttctgcc acaccgcggc gtatccgaag ccagttgacg tgaacacgca ccacgctg      1380 ccggacttca ttatgaaccg tggcggtgtg tcgctgcgtc cgggtgacgg cgtcattcac    1440
tcctggctga accgtatgct gctgccggat accgtcggta ccgtggtga ctcccatacc     1500 cgtttcccga tcggtatctc tttcccggcg ggttctggtc tggtggcgtt tgctgccgca    1560
```

```
actggcgtaa tgccgcttga tatgccggaa tccgttctgg tgcgcttcaa aggcaaaatg    1620
cagccgggca tcaccctgcg cgatctggta cacgctattc cgctgtatgc gatcaaacaa    1680
ggtctgctga ccgttgagaa gaaaggcaag aaaaacatct ctctggccg catcctggaa     1740 attgaaggtc tgccggatct gaaagttgag caggcctttg agctaaccga tgcgtccgcc    1800
gagcgttctg ccgctggttg taccatcaag ctgaacaaag aaccgatcat cgaatacctg    1860
aactctaaca tcgtcctgct gaagtggatg atcgcggaag gttacggcga tcgtcgtacc    1920
ctggaacgtc gtattcaggg catggaaaaa tggctggcga atcctgagct gctggaagcc    1980
gatgcagatg cggaatacgc ggcagtgatc gacatcgatc tggcggatat taaagagcca    2040
atcctgtgtg ctccgaacga cccggatgac gcgcgtccgc tgtctgcggt acagggtgag    2100
aagatcgacg aagtgtttat cggttcctgc atgaccaaca tcggtcactt ccgtgctgcg    2160
ggtaaactgc tggatgcgca taaaggtcag ttgccgaccc gctgtgggt ggcaccgcca     2220 acccgtatgg acgccgcaca gttgaccgaa gaaggctact acagcgtctt cggtaagagt    2280
ggtgcgcgta tcgagatccc tggctgttcc ctgtgtatgg gtaaccaggc gcgtgtggcg    2340
gacggtgcaa cggtggtttc cacctctacc cgtaacttcc cgaaccgtct gggtactggc    2400
gcgaatgtct tcctggcttc tgcggaactg gcggctgttg cggcgctgat tggcaaactg    2460
ccgacgccgg aagagtacca gacctacgtg gcgcaggtag ataaaacagc cgttgatact    2520
taccgttatc tgaacttcaa ccagctttct cagtacaccg agaaagccga tggggtgatt    2580
ttccagactg cggtttaa                                                  2598
```

<210> SEQ ID NO 10
<211> LENGTH: 865
<212> TYPE: PRT
<213> ORGANISM: Escherichia coli

<400> SEQUENCE: 10

```
Met Leu Glu Glu Tyr Arg Lys His Val Ala Glu Arg Ala Ala Glu Gly
1               5                   10                  15

Ile Ala Pro Lys Pro Leu Asp Ala Asn Gln Met Ala Ala Leu Val Glu
            20                  25                  30

Leu Leu Lys Asn Pro Pro Ala Gly Glu Glu Phe Leu Leu Asp Leu
        35                  40                  45

Leu Thr Asn Arg Val Pro Pro Gly Val Asp Glu Ala Ala Tyr Val Lys
    50                  55                  60

Ala Gly Phe Leu Ala Ala Ile Ala Lys Gly Glu Ala Lys Ser Pro Leu
65                  70                  75                  80

Leu Thr Pro Glu Lys Ala Ile Glu Leu Leu Gly Thr Met Gln Gly Gly
                85                  90                  95

Tyr Asn Ile His Pro Leu Ile Asp Ala Leu Asp Ala Lys Leu Ala
            100                 105                 110

Pro Ile Ala Ala Lys Ala Leu Ser His Thr Leu Leu Met Phe Asp Asn
        115                 120                 125

Phe Tyr Asp Val Glu Glu Lys Ala Lys Ala Gly Asn Glu Tyr Ala Lys
    130                 135                 140

Gln Val Met Gln Ser Trp Ala Asp Ala Glu Trp Phe Leu Asn Arg Pro
145                 150                 155                 160

Ala Leu Ala Glu Lys Leu Thr Val Thr Val Phe Lys Val Thr Gly Glu
                165                 170                 175

Thr Asn Thr Asp Asp Leu Ser Pro Ala Pro Asp Ala Trp Ser Arg Pro
            180                 185                 190
```

```
Asp Ile Pro Leu His Ala Leu Ala Met Leu Lys Asn Ala Arg Glu Gly
        195                 200                 205

Ile Glu Pro Asp Gln Pro Gly Val Val Gly Pro Ile Lys Gln Ile Glu
    210                 215                 220

Ala Leu Gln Gln Lys Gly Phe Pro Leu Ala Tyr Val Gly Asp Val Val
225                 230                 235                 240

Gly Thr Gly Ser Ser Arg Lys Ser Ala Thr Asn Ser Val Leu Trp Phe
                245                 250                 255

Met Gly Asp Asp Ile Pro His Val Pro Asn Lys Arg Gly Gly Gly Leu
            260                 265                 270

Cys Leu Gly Gly Lys Ile Ala Pro Ile Phe Phe Asn Thr Met Glu Asp
        275                 280                 285

Ala Gly Ala Leu Pro Ile Glu Val Asp Val Ser Asn Leu Asn Met Gly
        290                 295                 300

Asp Val Ile Asp Val Tyr Pro Tyr Lys Gly Glu Val Arg Asn His Glu
305                 310                 315                 320

Thr Gly Glu Leu Leu Ala Thr Phe Glu Leu Lys Thr Asp Val Leu Ile
                325                 330                 335

Asp Glu Val Arg Ala Gly Gly Arg Ile Pro Leu Ile Ile Gly Arg Gly
            340                 345                 350

Leu Thr Thr Lys Ala Arg Glu Ala Leu Gly Leu Pro His Ser Asp Val
        355                 360                 365

Phe Arg Gln Ala Lys Asp Val Ala Glu Ser Asp Arg Gly Phe Ser Leu
        370                 375                 380

Ala Gln Lys Met Val Gly Arg Ala Cys Gly Val Lys Gly Ile Arg Pro
385                 390                 395                 400

Gly Ala Tyr Cys Glu Pro Lys Met Thr Ser Val Gly Ser Gln Asp Thr
                405                 410                 415

Thr Gly Pro Met Thr Arg Asp Glu Leu Lys Asp Leu Ala Cys Leu Gly
            420                 425                 430

Phe Ser Ala Asp Leu Val Met Gln Ser Phe Cys His Thr Ala Ala Tyr
        435                 440                 445

Pro Lys Pro Val Asp Val Asn Thr His His Thr Leu Pro Asp Phe Ile
        450                 455                 460

Met Asn Arg Gly Gly Val Ser Leu Arg Pro Gly Asp Gly Val Ile His
465                 470                 475                 480

Ser Trp Leu Asn Arg Met Leu Leu Pro Asp Thr Val Gly Thr Gly Gly
                485                 490                 495

Asp Ser His Thr Arg Phe Pro Ile Gly Ile Ser Phe Pro Ala Gly Ser
            500                 505                 510

Gly Leu Val Ala Phe Ala Ala Thr Gly Val Met Pro Leu Asp Met
        515                 520                 525

Pro Glu Ser Val Leu Val Arg Phe Lys Gly Lys Met Gln Pro Gly Ile
        530                 535                 540

Thr Leu Arg Asp Leu Val His Ala Ile Pro Leu Tyr Ala Ile Lys Gln
545                 550                 555                 560

Gly Leu Leu Thr Val Glu Lys Lys Gly Lys Lys Asn Ile Phe Ser Gly
                565                 570                 575

Arg Ile Leu Glu Ile Glu Gly Leu Pro Asp Leu Lys Val Glu Gln Ala
            580                 585                 590

Phe Glu Leu Thr Asp Ala Ser Ala Glu Arg Ser Ala Ala Gly Cys Thr
        595                 600                 605

Ile Lys Leu Asn Lys Glu Pro Ile Ile Glu Tyr Leu Asn Ser Asn Ile
```

-continued

```
                610                 615                 620
Val Leu Leu Lys Trp Met Ile Ala Glu Gly Tyr Gly Asp Arg Arg Thr
625                 630                 635                 640

Leu Glu Arg Arg Ile Gln Gly Met Glu Lys Trp Leu Ala Asn Pro Glu
                645                 650                 655

Leu Leu Glu Ala Asp Ala Asp Ala Glu Tyr Ala Ala Val Ile Asp Ile
                660                 665                 670

Asp Leu Ala Asp Ile Lys Glu Pro Ile Leu Cys Ala Pro Asn Asp Pro
                675                 680                 685

Asp Asp Ala Arg Pro Leu Ser Ala Val Gln Gly Glu Lys Ile Asp Glu
                690                 695                 700

Val Phe Ile Gly Ser Cys Met Thr Asn Ile Gly His Phe Arg Ala Ala
705                 710                 715                 720

Gly Lys Leu Leu Asp Ala His Lys Gly Gln Leu Pro Thr Arg Leu Trp
                725                 730                 735

Val Ala Pro Pro Thr Arg Met Asp Ala Ala Gln Leu Thr Glu Glu Gly
                740                 745                 750

Tyr Tyr Ser Val Phe Gly Lys Ser Gly Ala Arg Ile Glu Ile Pro Gly
                755                 760                 765

Cys Ser Leu Cys Met Gly Asn Gln Ala Arg Val Ala Asp Gly Ala Thr
                770                 775                 780

Val Val Ser Thr Ser Thr Arg Asn Phe Pro Asn Arg Leu Gly Thr Gly
785                 790                 795                 800

Ala Asn Val Phe Leu Ala Ser Ala Glu Leu Ala Ala Val Ala Ala Leu
                805                 810                 815

Ile Gly Lys Leu Pro Thr Pro Glu Glu Tyr Gln Thr Tyr Val Ala Gln
                820                 825                 830

Val Asp Lys Thr Ala Val Asp Thr Tyr Arg Tyr Leu Asn Phe Asn Gln
                835                 840                 845

Leu Ser Gln Tyr Thr Glu Lys Ala Asp Gly Val Ile Phe Gln Thr Ala
                850                 855                 860

Val
865
```

PRODUCING ITACONIC ACID IN YEAST USING GLYCEROL AS THE SUBSTRATE

BACKGROUND OF THE INVENTION

Itaconic acid ("IA"), in high demand in the chemical industry, is a precursor compound commonly used in manufacture of various products, such as acrylic fibers, rubbers, artificial diamonds, and lens. Certain filamentous fungi (e.g., *Ustilago, Helicobasidium*, and *Aspergillus*) converts monosaccharide to this compound. It has been found that cis-aconitic acid decaroxylase ("CAD") plays a key role in the biosynthesis of IA.

SUMMARY OF THE INVENTION

The present invention is based on the unexpected discovery that genetically modified *Yarrowia lipolytica* cells expressing a CAD produces a high level of IA when cultured in a medium containing glycerol.

Accordingly, this invention features a method of producing IA in yeast using glycerol as the substrate. This method includes (i) providing a genetically modified yeast host cell that contains a first expression cassette including a yeast promoter operably linked to a nucleotide sequence encoding a CAD, (ii) culturing the yeast host cell in a medium containing glycerol at a concentration of 5 to 700 g/L (e.g., 5 to 250 g/L) under suitable conditions permitting conversion of glycerol to IA, and (iii) collecting the medium for isolation of the IA. In this method, the glycerol can be the sole substrate for IA synthesis. The yeast host cell (e.g., a *Y. lipolytica* cell) can further contain a second expression cassette and optionally a third expression cassette, each of which includes a yeast promoter operatively linked to a nucleotide sequence encoding a citrate synthase ("CS") or an aconitase ("Aco"). Any of the yeast promoters mentioned above can be hp4d, pTEF, pRPS7, or pG3P. Each of the three expression cassettes can include a leader sequence upstream to and in-frame with the nucleotide sequence encoding CAD, CS, or Aco. In one example, the leader sequence encodes the amino acid sequence of MSAILSTTSKSFLSRGSTRQCQNMQKAL-FALLNARHYS (SEQ ID NO:1). In another example, it encodes MKLATAFTILTAVLA (SEQ ID NO:2).

Also within the scope of this invention is a nucleic acid including a first, a second, and optionally, a third expression cassettes, each of which contains a yeast promoter in operative linkage with a nucleotide sequence encoding an enzyme involved in IA synthesis. In one example, the nucleic acid contains two expression cassettes, the first expression cassette encoding a CAD and the second encoding a CS or an Aco. In another example, the nucleic acid contains three expression cassettes encoding a CAD, a CS, and an Aco.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

DETAILED DESCRIPTION OF THE INVENTION

Figure 1:
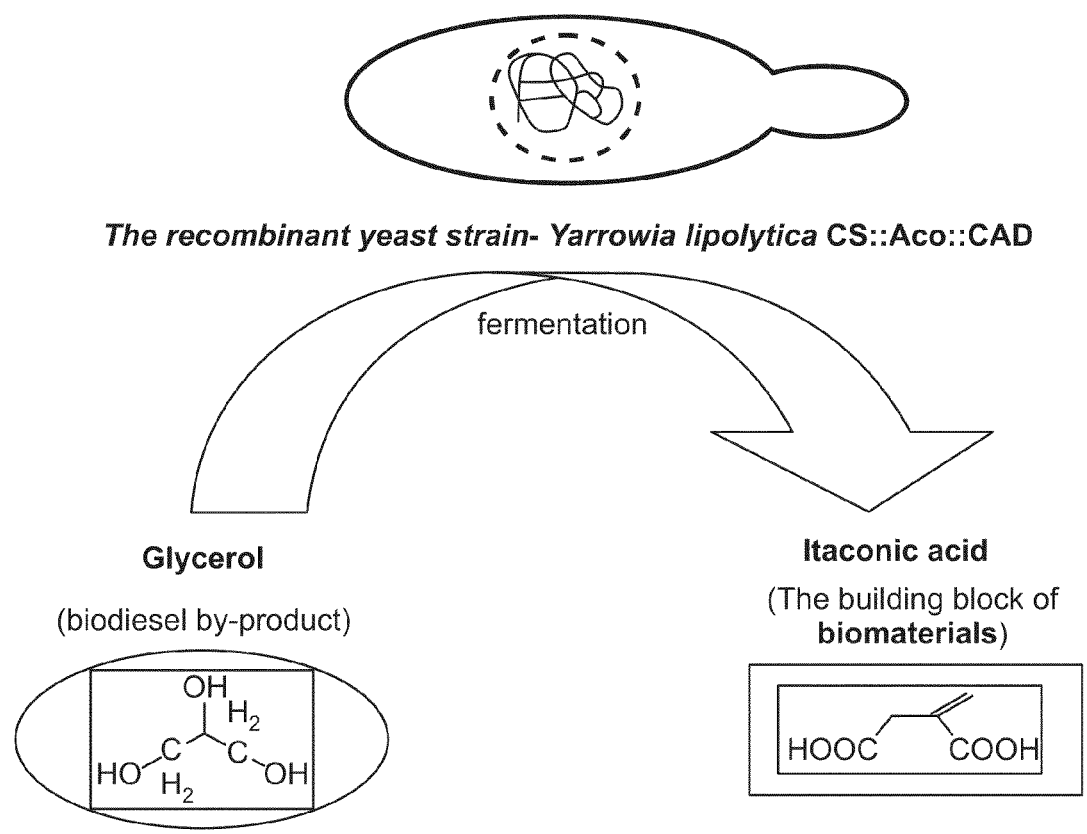
FIG. 1 is a diagram showing conversion of glycerol to IA in genetically modified *Y. lipolytica* cells that expresses a CAD, a CS, and an Aco.

Described herein is a method of producing IA in a genetically engineered yeast using glycerol as the substrate. See FIG. 1.

The genetically modified yeast (e.g., *Saccharomyces cerevisiae, Saccharomyces pombe, Yarrowia lipolytica, Pichia pastoris, Kluyveromyces lactis*, and *Pseudozyma antarctica*) is designed to express CAD, and optionally CS and/or Aco at a high level(s).

The term "cis-aconitic acid decarboxylase" or "CAD" used herein refers to a naturally occurring CAD (e.g., the *A. terreus* CAD described in Dwiarti et al., J. Bioscience and Bioengineering, 94 (1):29-33, 2002 and WO 2009/014437) and functional equivalents thereof. Provided below are the nucleotide sequence and amino acid sequence of an exemplary *A. terreus* CAD:

```
A. terreus Cis-aconitic Acid Decarboxylase
atgaccaagcagtctgctgattccaacgcgaagtctggtgtgacctc
 M  T  K  Q  S  A  D  S  N  A  K  S  G  V  T  S tgagatctgtcactgggcgtctaatctcgccactgatgatatcccga
 E  I  C  H  W  A  S  N  L  A  T  D  D  I  P gcgacgttctggagcgtgcaaaatacctgatcctggatggtatcgcg
 S  D  V  L  E  R  A  K  Y  L  I  L  D  G  I  A tgcgcgtgggtaggtgctcgtgtcccatggtctgaaaaatacgttca
 C  A  W  V  G  A  R  V  P  W  S  E  K  Y  V  Q agcgaccatgtctttcgaacctccgggtgcgtgtcgtgtcatcggtt
    A  T  M  S  F  E  P  P  G  A  C  R  V  I  G acggccagaaactgggtccggtagcggctgccatgacgaactctgca
 Y  G  Q  K  L  G  P  V  A  A  A  M  T  N  S  A tttattcaggcgaccgaactcgatgactatcactctgaagcgccgct
 F  I  Q  A  T  E  L  D  D  Y  H  S  E  A  P  L gcattccgcgtctatcgttctcccggcagttttcgcggcgagcgaag
 H  S  A  S  I  V  L  P  A  V  F  A  A  S  E tactggccgaacagggtaaaaccatctctggtattgacgtgattctg
 V  L  A  E  Q  G  K  T  I  S  G  I  D  V  I  L gctgcgatcgttggtttcgagagcggtcctcgcatcggcaaagcgat
 A  A  I  V  G  F  E  S  G  P  R  I  G  K  A  I ctacggttctgacctcctgaacaacggctggcactgcggtgcggtat
 Y  G  S  D  L  L  N  N  G  W  H  C  G  A  V atggcgcaccggctggtgcgctcgcaactggtaagctcctgggcctc
 Y  G  A  P  A  G  A  L  A  T  G  K  L  L  G  L acgccggacagcatggaagatgcactgggtattgcctgcacgcaagc
 T  P  D  S  M  E  D  A  L  G  I  A  C  T  Q  A atgcggcctcatgtccgcgcagtatggtggcatggttaaacgtgttc
 C  G  L  M  S  A  Q  Y  G  G  M  V  K  R  V agcacggtttcgcagcgcgtaatggtctcctcggtggcctcctggct
 Q  H  G  F  A  A  R  N  G  L  L  G  G  L  L  A cacggcggctacgaggcgatgaaaggtgttctcgagcgttcttacgg
 H  G  G  Y  E  A  M  K  G  V  L  E  R  S  Y  G
```

```
tggcttcctgaagatgttcaccaagggcaacggtcgtgaaccgccgt
 G  F  L  K  M  F  T  K  G  N  G  R  E  P  P acaaagaagaagaggttgtggctggtctgggtagcttctggcacacc
 Y  K  E  E  E  V  V  A  G  L  G  S  F  W  H  T ttcaccattcgtatcaaactgtacgcgtgctgcggtctcgtacacgg
 F  T  I  R  I  K  L  Y  A  C  C  G  L  V  H  G tcctgttgaagccattgaaaacctccagggtcgttacccggaactgc
 P  V  E  A  I  E  N  L  Q  G  R  Y  P  E  L tcaatcgtgctaacctgtctaacatccgccacgttcacgtacaactc
 L  N  R  A  N  L  S  N  I  R  H  V  H  V  Q  L tctaccgcgagcaactcccactgtggttggatcccagaagagcgccc
 S  T  A  S  N  S  H  C  G  W  I  P  E  E  R  P aatctcttctatcgcgggtcaaatgtctgtcgcatatatcctcgccg
 I  S  S  I  A  G  Q  M  S  V  A  Y  I  L  A ttcagctcgttgaccaacagtgtctgctcagccagttctccgagttt
 V  Q  L  V  D  Q  Q  C  L  L  S  Q  F  S  E  F gacgataatctggaacgcccggaagtgtgggacctggcacgtaaggt
 D  D  N  L  E  R  P  E  V  W  D  L  A  R  K  V taccagctctcaatctgaggagttcgaccaggacggtaactgtctct
 T  S  S  Q  S  E  E  F  D  Q  D  G  N  C  L ctgccggtcgcgtccgtattgagttcaacgacggctcctccatcacc
 S  A  G  R  V  R  I  E  F  N  D  G  S  S  I  T gaatccgttgagaagccgctcggtgtaaaggaaccaatgccaaatga
 E  S  V  E  K  P  L  G  V  K  E  P  M  P  N  E acgcatcctgcacaaataccgtaccctggcgggttctgtaacggacg
 R  I  L  H  K  Y  R  T  L  A  G  S  V  T  D aaagccgtgttaaggagatcgaggatctcgtgctcggcctggaccgt
 E  S  R  V  K  E  I  E  D  L  V  L  G  L  D  R ctgaccgatattagcccgctcctcgagctgctgaattgtccggttaa
 L  T  D  I  S  P  L  L  E  L  L  N  C  P  V  K atccccactggtttaa (SEQ ID NO: 3)
 S  P  L  V  -   (SEQ ID NO: 4)
```

The terms "citrate synthase" and "aconitase" used herein refer to enzymes that convert oxaloacetate to citrate and convert citrate or isocitrate to cis-aconitic acid, respectively, including both naturally-occurring enzymes and their functional equivalents. Provided below are nucleotide sequences and amino acid sequences of *E. coli* citrate synthase, aconitase A, and aconitase B:

*E. coli* Citrate Synthase
```
atggctgatacaaaagcaaaactcaccctcaacggggatacagctgt
 M  A  D  T  K  A  K  L  T  L  N  G  D  T  A  V tgaactggatgtgctgaaaggcacgctgggtcaagatgttattgata
 E  L  D  V  L  K  G  T  L  G  Q  D  V  I  D tccgtactctcggttcaaaaggtgtgttcacctttgacccaggcttc
 I  R  T  L  G  S  K  G  V  F  T  F  D  P  G  F acttcaaccgcatcctgcgaatctaaaattacttttattgatggtga
 T  S  T  A  S  C  E  S  K  I  T  F  I  D  G  D tgaaggtattttgctgcaccgcgggtttccgatcgatcagctggcga
 E  G  I  L  L  H  R  G  F  P  I  D  Q  L  A ccgattctaactacctggaagtttgttacatcctgctgaatggtgaa
 T  D  S  N  Y  L  E  V  C  Y  I  L  L  N  G  E aaaccgactcaggaacagtatgacgaatttaaaactacggtgacccg
 K  P  T  Q  E  Q  Y  D  E  F  K  T  T  V  T  R tcataccatgatccacgagcagattaccgtctgttccatgctttcc
 H  T  M  I  H  E  Q  I  T  R  L  F  H  A  F gtcgcgactcgcatccaatggcagtcatgtgtggtattaccggcgcg
 R  R  D  S  H  P  M  A  V  M  C  G  I  T  G  A ctggcggcgttctatcacgactcgctggatgttaacaatcctcgtca
 L  A  A  F  Y  H  D  S  L  D  V  N  N  P  R  H ccgtgaaattgccgcgttccgcctgctgtcgaaaatgccgaccatgg
 R  E  I  A  A  F  R  L  L  S  K  M  P  T  M ccgcgatgtgttacaagtattccattggtcagccatttgtttacccg
 A  A  M  C  Y  K  Y  S  I  G  Q  P  F  V  Y  P cgcaacgatctctcctacgccggtaacttcctgaatatgatgttctc
 R  N  D  L  S  Y  A  G  N  F  L  N  M  M  F  S cacgccgtgcgaaccgtatgaagttaatccgattctggaacgtgcta
 T  P  C  E  P  Y  E  V  N  P  I  L  E  R  A tggaccgtattctgatcctgcacgctgaccatgaacagaacgcctct
 M  D  R  I  L  I  L  H  A  D  H  E  Q  N  A  S acctccaccgtgcgtaccgctggctcttcgggtgcgaacccgtttgc
 T  S  T  V  R  T  A  G  S  S  G  A  N  P  F  A ctgtatcgcagcaggtattgcttcactgtggggacctgcgcacggcg
 C  I  A  A  G  I  A  S  L  W  G  P  A  H  G gtgctaacgaagcggcgctgaaaatgctggaagaaatcagctccgtt
 G  A  N  E  A  A  L  K  M  L  E  E  I  S  S  V aaacacattccggaatttgttcgtcgtgcgaaagacaaaaatgattc
 K  H  I  P  E  F  V  R  R  A  K  D  K  N  D  S tttccgcctgatgggcttcggtcaccgcgtgtacaaaaattacgacc
 F  R  L  M  G  F  G  H  R  V  Y  K  N  Y  D gcgcgccaccgtaatgcgtgaaacctgccatgaagtgctgaaagag
 P  R  A  T  V  M  R  E  T  C  H  E  V  L  K  E ctgggcacgaaggatgacctgctggaagtggctatggagctggaaaa
 L  G  T  K  D  D  L  L  E  V  A  M  E  L  E  N catcgcgctgaacgacccgtactttatcgagaagaaactgtacccga
 I  A  L  N  D  P  Y  F  I  E  K  K  L  Y  P acgtcgatttctactctggtatcatcctgaaagcgatgggtattccg
 N  V  D  F  Y  S  G  I  I  L  K  A  M  G  I  P tcttccatgttcaccgtcattttcgcaatggcacgtaccgttggctg
 S  S  M  F  T  V  I  F  A  M  A  R  T  V  G  W gatcgcccactggagcgaaatgcacagtgacggtatgaagattgccc
 I  A  H  W  S  E  M  H  S  D  G  M  K  I  A gtccgcgtcagctgtatacaggatatgaaaaacgcgactttaaaagc
 R  P  R  Q  L  Y  T  G  Y  E  K  R  D  F  K  S gatatcaagcgttaa (SEQ ID NO: 5)
 D  I  K  R  -   (SEQ ID NO: 6)
```

*E. coli* Aconitase A
```
atgtcgtcaacccctacgagaagccagtaaggacacgttgcaggccaa
 M  S  S  T  L  R  E  A  S  K  D  T  L  Q  A  K agataaaacttaccactactacagcctgccgcttgctgctaaatcac
 D  K  T  Y  H  Y  Y  S  L  P  L  A  A  K  S tgggcgatatcacccgtctacccaagtcactcaaagttttgctcgaa
 L  G  D  I  T  R  L  P  K  S  L  K  V  L  L  E aacctgctgcgctggcaggatggtaactcggttaccgaagaggatat
 N  L  L  R  W  Q  D  G  N  S  V  T  E  E  D  I ccacgcgctggcaggatggctgaaaaatgcccatgctgaccgtgaaa
 H  A  L  A  G  W  L  K  N  A  H  A  D  R  E
```

```
ttgcctaccgcccggcaagggtgctgatgcaggactttaccggcgta
 I  A  Y  R  P  A  R  V  L  M  Q  D  F  T  G  V cctgccgttgttgatctggcggcaatgcgcgaagcggttaaacgcct
 P  A  V  V  D  L  A  A  M  R  E  A  V  K  R  L cggcggcgatactgcaaaggttaacccgctctcaccggtcgacctgg
 G  G  D  T  A  K  V  N  P  L  S  P  V  D  L tcattgaccactcggtgaccgtcgatcgttttggtgatgatgaggca
 V  I  D  H  S  V  T  V  D  R  F  G  D  D  E  A tttgaagaaaacgtacgcctggaaatgggagcgcaaccacgaacgtta
 F  E  E  N  V  R  L  E  M  E  R  N  H  E  R  Y tgtgttcctgaaatggggaaagcaagcgttcagtcggtttagcgtcg
 V  F  L  K  W  G  K  Q  A  F  S  R  F  S  V tgccgccaggcacaggcatttgccatcaggttaacctcgaatatctc
 V  P  P  G  T  G  I  C  H  Q  V  N  L  E  Y  L ggcaaagcagtgtggagtgaattgcaggacggtgaatggattgctta
 G  K  A  V  W  S  E  L  Q  D  G  E  W  I  A  Y tccggatacactcgttggtactgactcgcacaccaccatgatcaacg
 P  D  T  L  V  G  T  D  S  H  T  T  M  I  N gccttggcgtgctggggtggggcgttggtgggatcgaagcagaagcc
 G  L  G  V  L  G  W  G  V  G  G  I  E  A  E  A gcaatgttaggccagccggtttccatgcttatcccggatgtagtggg
 A  M  L  G  Q  P  V  S  M  L  I  P  D  V  V  G cttcaaacttaccggaaaattacgtgaaggtattaccgccacagacc
 F  K  L  T  G  K  L  R  E  G  I  T  A  T  D tggttctcactgttacccaaatgctgcgcaaacatggcgtggtgggg
 L  V  L  T  V  T  Q  M  L  R  K  H  G  V  V  G aaattcgtcgaattttatggtgatggtctggattcactaccgttggc
 K  F  V  E  F  Y  G  D  G  L  D  S  L  P  L  A ggatcgcgccaccattgccaatatgtcgccagaatatggtgccacct
 D  R  A  T  I  A  N  M  S  P  E  Y  G  A  T gtggcttcttcccaatcgatgctgtaaccctcgattacatgcgttta
 C  G  F  F  P  I  D  A  V  T  L  D  Y  M  R  L agcgggcgcagcgaagatcaggtcgagttggtcgaaaaatatgccaa
 S  G  R  S  E  D  Q  V  E  L  V  E  K  Y  A  K agcgcagggcatgtggcgtaacccgggcgatgaaccaatttttacca
 A  Q  G  M  W  R  N  P  G  D  E  P  I  F  T gtacgttagaactggatatgaatgacgttgaagcgagcctggcaggg
 S  T  L  E  L  D  M  N  D  V  E  A  S  L  A  G cctaaacgcccacaggatcgcgttgcactgcccgatgtaccaaaagc
 P  K  R  P  Q  D  R  V  A  L  P  D  V  P  K  A atttgccgccagtaacgaactggaagtgaatgccacgcataaagatc
 F  A  A  S  N  E  L  E  V  N  A  T  H  K  D gccagccggtcgattatgttatgaacggacatcagtatcagttacct
 R  Q  P  V  D  Y  V  M  N  G  H  Q  Y  Q  L  P gatggcgctgtggtcattgctgcgataacctcgtgcaccaacacctc
 D  G  A  V  V  I  A  A  I  T  S  C  T  N  T  S taacccaagtgtgctgatgccgcaggcttgctggcgaaaaaagccg
 N  P  S  V  L  M  A  A  G  L  L  A  K  K  A taactctgggcctcaagcggcaaccatgggtcaaagcgtcgctggca
 V  T  L  G  L  K  R  Q  P  W  V  K  A  S  L  A ccggggtcgaaagtcgtttctgattatctggcaaaagcgaaactgac
 P  G  S  K  V  V  S  D  Y  L  A  K  A  K  L  T accgtatctcgacgaactggggtttaaccttgtgggatacggttgta
 P  Y  L  D  E  L  G  F  N  L  V  G  Y  G  C ccacctgtattggtaactctgggccgctgccgatcctatcgaaacg
 T  T  C  I  G  N  S  G  P  L  P  D  P  I  E  T gcaatcaaaaaaagcgatttaaccgtcggtgcggtgctgtccggcaa
 A  I  K  K  S  D  L  T  V  G  A  V  L  S  G  N ccgtaactttgaaggccgtatccatccgctggttaaaactaactggc
 R  N  F  E  G  R  I  H  P  L  V  K  T  N  W tggcctcgccgccgctggtggttgcctatgcgctggcgggaaatatg
 L  A  S  P  P  L  V  V  A  Y  A  L  A  G  N  M aatatcaacctggcttctgagcctatcggccatgatcgcaaaggcga
 N  I  N  L  A  S  E  P  I  G  H  D  R  K  G  D tccggtttatctgaaagatatctggccatcggcacaagaaattgccc
 P  V  Y  L  K  D  I  W  P  S  A  Q  E  I  A gtgcggtagaacaagtctccacagaaatgttccgcaaagagtacgca
 R  A  V  E  Q  V  S  T  E  M  F  R  K  E  Y  A gaagttttgaaggcacagcagagtggaagggaattaacgtcacacg
 E  V  F  E  G  T  A  E  W  K  G  I  N  V  T  R atccgataccttacggttggcaggaggactcaacctatattcgcttat
 S  D  T  Y  G  W  Q  E  D  S  T  Y  I  R  L cgcctttcttttgatgaaatgcaggcaacaccagcaccagtggaagat
 S  P  F  F  D  E  M  Q  A  T  P  A  P  V  E  D attcacggtgcgcggatcctcgcaatgctggggggattcagtcaccac
 I  H  G  A  R  I  L  A  M  L  G  D  S  V  T  T tgaccatatctctccggcgggcagtattaagcccgacagcccagcgg
 D  H  I  S  P  A  G  S  I  K  P  D  S  P  A gtcgatatctacaaggtcggggtgttgagcgaaaagactttaactcc
 G  R  Y  L  Q  G  R  G  V  E  R  K  D  F  N  S tacggttcgcggcgtggtaaccatgaagtgatgatgcgcggcacctt
 Y  G  S  R  R  G  N  H  E  V  M  M  R  G  T  F cgccaatattcgcatccgtaatgaaatggtgcctggcgttgaagggg
 A  N  I  R  I  R  N  E  M  V  P  G  V  E  G ggatgacgcgcatttacctgacagcgacgtagtctctatttatgat
 G  M  T  R  H  L  P  D  S  D  V  V  S  I  Y  D gctgcgatgcgctataagcaggagcaaacgccgctggcggtgattgc
 A  A  M  R  Y  K  Q  E  Q  T  P  L  A  V  I  A cgggaaagagtatggatcaggctccagtcgtgactgggcggcaaaag
 G  K  E  Y  G  S  G  S  S  R  D  W  A  A  K gtccgcgtctgcttggtattcgtgtggtgattgccgaatcgtttgaa
 G  P  R  L  L  G  I  R  V  V  I  A  E  S  F  E cgaattcaccgttcgaatttaattggcatgggcatcctgccgctgga
 R  I  H  R  S  N  L  I  G  M  G  I  L  P  L  E atttccgcaaggcgtaacgcgtaaaacgttagggctaaccggggaag
 F  P  Q  G  V  T  R  K  T  L  G  L  T  G  E agaagattgatattggcgatctgcaaaacctacaacccggcgcgacg
 E  K  I  D  I  G  D  L  Q  N  L  Q  P  G  A  T gttccggtgacgcttacgcgcgcggatggtagccaggaagtcgtacc
 V  P  V  T  L  T  R  A  D  G  S  Q  E  V  V  P ctgccgttgtcgtatcgacaccgcgacggagttgacctactaccaga
 C  R  C  R  I  D  T  A  T  E  L  T  Y  Y  Q acgacggcattttgcattatgtcattcgtaatatgttgaagtaa
 N  D  G  I  L  H  Y  V  I  R  N  M  L  K  -

(SEQ ID NO: 7)
(SEQ ID NO: 8)
```

E. coli Aconitase B

```
atgctagaagaataccgtaagcacgtagctgagcgtgccgctgaggg
 M  L  E  E  Y  R  K  H  V  A  E  R  A  A  E  G gattgcgcccaaaccctggatgcaaaccaaatggccgcacttgtag
 I  A  P  K  P  L  D  A  N  Q  M  A  A  L  V agctgctgaaaaacccgcccgcgggcgaagaagaattcctgttagat
 E  L  L  K  N  P  P  A  G  E  E  E  F  L  L  D ctgttaaccaaccgtgttccccaggcgtcgatgaagccgcctatgt
 L  L  T  N  R  V  P  P  G  V  D  E  A  A  Y  V caaagcaggcttcctggctgctatcgcgaaaggcgaagccaaatccc
 K  A  G  F  L  A  A  I  A  K  G  E  A  K  S ctctgctgactccggaaaaagccatcgaactgctgggcaccatgcag
 P  L  L  T  P  E  K  A  I  E  L  L  G  T  M  Q ggtggttacaacattcatccgctgatcgacgcgctggatgatgccaa
 G  G  Y  N  I  H  P  L  I  D  A  L  D  D  A  K actggcacctattgctgccaaagcactttctcacacgctgctgatgt
 L  A  P  I  A  A  K  A  L  S  H  T  L  L  M tcgataacttctatgacgtagaagagaaagcgaaagcaggcaacgaa
 F  D  N  F  Y  D  V  E  E  K  A  K  A  G  N  E tatgcgaagcaggttatgcagtcctgggcggatgccgaatggttcct
 Y  A  K  Q  V  M  Q  S  W  A  D  A  E  W  F  L gaatcgcccggcgctggctgaaaaactgaccgttactgtcttcaaag
 N  R  P  A  L  A  E  K  L  T  V  T  V  F  K tcactggcgaaactaacaccgatgacctttctccggcaccggatgcg
 V  T  G  E  T  N  T  D  D  L  S  P  A  P  D  A tggtcacgcccggatatcccactgcacgcgctggcgatgctgaaaaa
 W  S  R  P  D  I  P  L  H  A  L  A  M  L  K  N cgccccgtgaaggtattgagccagaccagcctggtgttgttggtccga
 A  R  E  G  I  E  P  D  Q  P  G  V  V  G  P tcaagcaaatcgaagctctgcaacagaaagggtttcccgctggcgtac
 I  K  Q  I  E  A  L  Q  Q  K  G  F  P  L  A  Y gtcggtgacgttgtgggtacgggttcttcgcgtaaatccgccactaa
 V  G  D  V  V  G  T  G  S  S  R  K  S  A  T  N ctccgttctgtggtttatgggcgatgatattccacatgtgccgaaca
 S  V  L  W  F  M  G  D  D  I  P  H  V  P  N aacgcggcggtggtttgtgcctcggcggtaaaattgcacccatcttc
 K  R  G  G  G  L  C  L  G  G  K  I  A  P  I  F tttaacacgatggaagacgcgggtgcactgccaatcgaagtcgacg
 F  N  T  M  E  D  A  G  A  L  P  I  E  V  D  V ctctaacctgaacatgggcgacgtgattgacgtttacccgtacaaag
 S  N  L  N  M  G  D  V  I  D  V  Y  P  Y  K gtgaagtgcgtaaccacgaaaccggcgaactgctggcgaccttcgaa
 G  E  V  R  N  H  E  T  G  E  L  L  A  T  F  E ctgaaaaccgacgtgctgattgatgaagtgcgtgctggtggccgtat
 L  K  T  D  V  L  I  D  E  V  R  A  G  G  R  I tccgctgattatcgggcgtggcctgaccaccaaagcgcgtgaagcac
 P  L  I  I  G  R  G  L  T  T  K  A  R  E  A ttggtctgccgcacagtgatgtgttccgtcaggcgaaagatgtcgct
 L  G  L  P  H  S  D  V  F  R  Q  A  K  D  V  A gagagcgatcgcggcttctcgctggcgcaaaaaatggtaggccgtgc
 E  S  D  R  G  F  S  L  A  Q  K  M  V  G  R  A ctgtggcgtgaaaggcattcgtccgggcgcgtactgtgaaccgaaaa
 C  G  V  K  G  I  R  P  G  A  Y  C  E  P  K tgacttctgtaggttcccaggacaccaccggcccgatgacccgtgat
 M  T  S  V  G  S  Q  D  T  T  G  P  M  T  R  D gaactgaaagacctggcgtgcctgggcttctcggctgacctggtgat
 E  L  K  D  L  A  C  L  G  F  S  A  D  L  V  M gcagtctttctgccacaccgcggcgtatccgaagccagttgacgtga
 Q  S  F  C  H  T  A  A  Y  P  K  P  V  D  V acacgcaccacacgctgccggacttcattatgaaccgtggcggtgtg
 N  T  H  H  T  L  P  D  F  I  M  N  R  G  G  V tcgctgcgtccgggtgacggcgtcattcactcctggctgaaccgtat
 S  L  R  P  G  D  G  V  I  H  S  W  L  N  R  M gctgctgccggataccgtcggtaccggtggtgactcccatacccgtt
 L  L  P  D  T  V  G  T  G  G  D  S  H  T  R tcccgatcggtatctctttcccggcgggttctggtctggttggcgttt
 F  P  I  G  I  S  F  P  A  G  S  G  L  V  A  F gctgccgcaactggcgtaatgccgcttgatatgccggaatccgttct
 A  A  A  T  G  V  M  P  L  D  M  P  E  S  V  L ggtgcgcttcaaaggcaaaatgcagccgggcatcaccctgcgcgatc
 V  R  F  K  G  K  M  Q  P  G  I  T  L  R  D tggtacacgctattccgctgtatgcgatcaaacaaggtctgctgacc
 L  V  H  A  I  P  L  Y  A  I  K  Q  G  L  L  T gttgagaagaaaggcaagaaaaacatcttctctggccgcatcctgga
 V  E  K  K  G  K  K  N  I  F  S  G  R  I  L  E aattgaaggtctgccggatctgaaagttgagcaggcctttgagctaa
 I  E  G  L  P  D  L  K  V  E  Q  A  F  E  L ccgatgcgtccgccgagcgttctgccgctggttgtaccatcaagctg
 T  D  A  S  A  E  R  S  A  A  G  C  T  I  K  L aacaaagaaccgatcatcgaatacctgaactctaacatcgtcctgct
 N  K  E  P  I  I  E  Y  L  N  S  N  I  V  L  L gaagtggatgatcgcggaaggttacggcgatcgtcgtaccctggaac
 K  W  M  I  A  E  G  Y  G  D  R  R  T  L  E gtcgtattcagggcatggaaaaatggctggcgaatcctgagctgctg
 R  R  I  Q  G  M  E  K  W  L  A  N  P  E  L  L gaagccgatgcagatgcggaatacgcggcagtgatcgacatcgatct
 E  A  D  A  D  A  E  Y  A  A  V  I  D  I  D  L ggcggatatattaaagagccaatcctgtgtgctccgaacgaccggatg
 A  D  I  K  E  P  I  L  C  A  P  N  D  P  D acgcgcgtccgctgtctgcgcgtacagggtgagaagatcgacgaagtg
 D  A  R  P  L  S  A  V  Q  G  E  K  I  D  E  V tttatcggttcctgcatgaccaacatcggtcacttccgtgctgcggg
 F  I  G  S  C  M  T  N  I  G  H  F  R  A  A  G taaactgctggatgcgcataaaggtcagttgccgacccgcctgtggg
 K  L  L  D  A  H  K  G  Q  L  P  T  R  L  W tggcaccgccaacccgtatggacgccgcacagttgaccgaagaaggc
 V  A  P  P  T  R  M  D  A  A  Q  L  T  E  E  G tactacagcgtcttcggtaagagtggtgcgcgtatcgagatccctgg
 Y  Y  S  V  F  G  K  S  G  A  R  I  E  I  P  G ctgttccctgtgtatgggtaaccaggcgcgtgtggcggacggtgcaa
 C  S  L  C  M  G  N  Q  A  R  V  A  D  G  A cggtggtttccacctctacccgtaacttcccgaaccgtctgggtact
 T  V  V  S  T  S  T  R  N  F  P  N  R  L  G  T ggcgcgaatgtcttcctggcttctgcggaactggcggctgttgcggc
 G  A  N  V  F  L  A  S  A  E  L  A  A  V  A  A gctgattggcaaactgccgacgccggaagagtaccagacctacgtgg
 L  I  G  K  L  P  T  P  E  E  Y  Q  T  Y  V
```

-continued

```
cgcaggtagataaaacagccgttgatacttaccgttatctgaacttc
 A  Q  V  D  K  T  A  V  D  T  Y  R  Y  L  N  F aaccagctttctcagtacaccgagaaagccgatggggtgattttcca
 N  Q  L  S  Q  Y  T  E  K  A  D  G  V  I  F  Q gactgcggtttaa (SEQ ID NO: 9)
 T  A  V   -  (SEQ ID NO: 10)
```

Other examples of CS and Aco are listed in Table 1 below:

TABLE 1

GenBank Accession Numbers of Exemplary Citrate Synthase and Aconitase

| Enzymes | GenBank Accession Numbers |
| --- | --- |
| Citrate synthase | AAC73814 (*E. coli*); NP_001080194 (*X. laevis*); CAB66275 (*S. coelicolor*); NP_080720 (*M. musculus*); ABP36423 (*C. phaeovibrioides*); XP_001827205 (*A. oryzae*); EDN 61138 (*S. cerevisiae*); and CAB77625 (*A. niger*) |
| Aconitase | CAA90177 (*B. taurus*); CAQ017353 (*C. michiganesis*); CAC37548 (*S. coelicolor*); AAC46192 (*M. avium*); 1L5JB (*E. coli*); EDN59216 (*S. cerevisiae*); AAC61778 (*A. terreus*); YP_910600 (*C. phaeobacteroides*) |

As used herein, a functional equivalent of a reference enzyme (i.e., the *A. terreus* CAD or any of the enzymes mentioned below) is a polypeptide having an amino acid sequence at least 60% (e.g., 85%, 90%, 95%, or 99%) identical to that of the reference enzyme and possessing the same enzymatic activity as the reference enzyme.

The percent identity of two amino acid sequences is determined using the algorithm of Karlin and Altschul *Proc. Natl. Acad. Sci.* USA 87:2264-68, 1990, as modified in Karlin and Altschul *Proc. Natl. Acad. Sci. USA* 90:5873-77, 1993. Such an algorithm is incorporated into the BLASTN and BLASTX programs (version 2.0) of Altschul, et al. *J. Mol. Biol.* 215: 403-10, 1990. BLAST protein searches can be performed with the BLASTX program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25:3389-3402, 1997. When utilizing BLAST and Gapped BLAST programs, the default parameters of the respective programs (e.g., BLASTX and BLASTN) can be used.

The genetically engineered yeast used in the method of this invention can also be modified to express other enzymes involved in IA synthesis (e.g., phosphoenolpyruvate carboxylases/carboxykinase, 2-methylcitrate synthases, citrate lyases, and 2-methylcitrate dehydratase) or to knock out genes involved in IA degradation (e.g., the icd gene encoding isocitrate decarboxylase). See U.S. patent application Ser. No. 12/463,677 and WO 2009/014437.

The above-described genetically modified yeast can be constructed by conventional recombinant technology (see, e.g., Sambrook et al., Molecular Cloning: A Laboratory Manual, Cold Spring Harbor Laboratory Press.)

More specifically, a yeast strain that overly expresses one or more of the enzymes mentioned above can be obtained as follows. A DNA fragment(s) encoding the one or more of the enzymes can be obtained by polymerase chain reaction from its natural source(s) based on its coding sequence(s), which can be retrieved from GenBank. If desired, the coding sequences are subjected to codon optimization based on the optimal codon usage in yeast. Preferably, a leader sequence that encodes a signal peptide is linked in-frame with the coding sequence at its 5' end. A signal peptide is an N-terminal fragment of a polypeptide that facilitates transport of the polypeptide into or through the membrane or for its secretion into the extracellular medium. Examples of the leader sequence include, but are not limited to, sequences encoding the signal peptides of prepro-CS (MSAILSTTSKSFLSRG-STRQCQNMQKALFALLNARHYS; SEQ ID NO:1) and pre-XPR2 (MKLATAFTILTAVLA; SEQ ID NO:2).

The DNA fragment(s) thus prepared is then inserted into a suitable yeast expression vector to produce DNA construct(s) for expression of the enzyme(s) mentioned above. In the DNA construct(s) thus prepared, the DNA fragment(s) is operably linked to a suitable yeast promoter to form an expression cassette. In one example, one expression cassette includes one coding sequence operably linked to a promoter. In another example, one expression cassette includes multiple coding sequences, all of which are in operative linkage with a promoter.

As used herein, the term "yeast promoter" refers to a nucleotide sequence containing elements that initiate the transcription of an operably linked nucleic acid sequence in yeast. At a minimum, a promoter contains an RNA polymerase binding site. It can further contain one or more enhancer elements which, by definition, enhance transcription, or one or more regulatory elements that control the on/off status of the promoter. Exemplary yeast promoters include 3-phosphoglycerate kinase promoter, glyceraldehyde-3-phosphate dehydrogenase (GAPDH) promoter, galactokinase (GAL1) promoter, galactoepimerase promoter, alcohol dehydrogenase (ADH) promoter, hp4d promoter (see Nicad et al., FEMS Yeast Research 2(3):371-379, 2006), translation elongation factor 1-αpromoter (pTEF), ribosomal protein S7 prompter (pRPS7), and glycerol-3-phosphate dehydrogenase promoter (pG3P).

The expression cassette(s) described above, contained in one or more expression constructs, is then introduced into a suitable yeast cell to produce the genetically modified yeast disclosed herein. Positive transformants are selected and the over-expression of one or more of the enzymes mentioned above are confirmed by methods known in the art, e.g., immune-blotting or enzymatic activity analysis.

To produce IA, the modified yeast cells are cultured in a suitable medium containing glycerol at a concentration of 5-700 g/L. The glycerol can be the only substrate in the medium for IA production. After a sufficient culturing period, the medium is collected and the secreted itaconic acid is isolated. Preferably, clones of the modified yeast that grow fast in glycerol are selected as the strains used in IA production.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Example 1

Figure 2A:
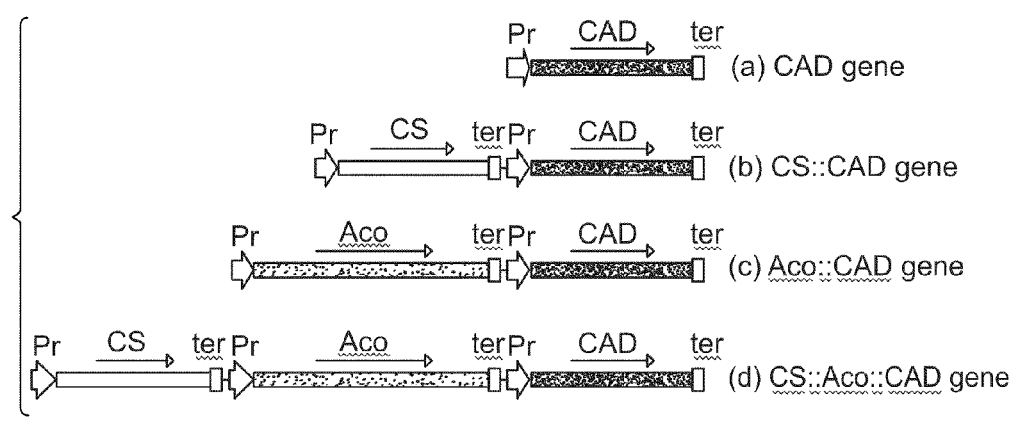
FIG. 2A is a diagram showing DNA cassettes for expression of CAD (cassette a), CAD and CS (cassette b), CAD and Aco (cassette c), and CAD, CS, and Aco (cassette d).
Figure 2B:
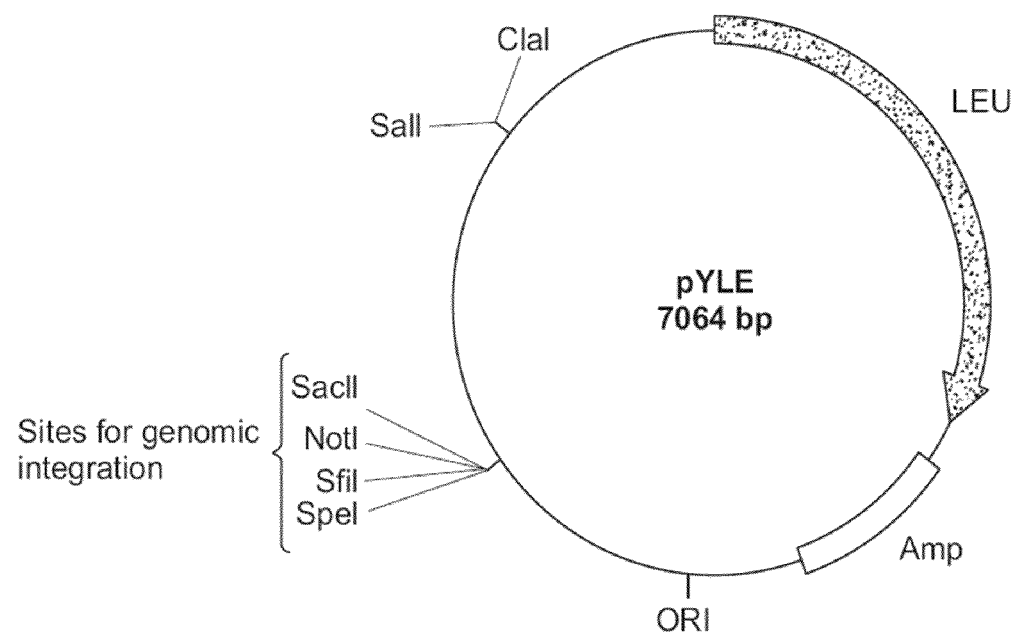
FIG. 2B is a map of expression vector pYLE. Sal I and Cla I are the restriction sites for cloning the cassettes mentioned above.

Construction of Expression Constructs for Producing CAD, CS, and Aco in *Yarrowia Lipolytica* Cells The DNA fragments (a), (b), (c), and (d) shown in FIG. 2A, were constructed via conventional recombinant technology. These fragments were cloned into vector pYLE via the Sal I and Cla I restriction sites to produce expression constructs suitable for expressing CAD, CS, and Aco in yeast cells. See FIG. 2B. The coding sequence(s) and the regulatory sequences i.e., promoter(s) and terminator(s), in these constructs are summarized in Table 2 below:

TABLE 2

Coding Sequence(s) and Regulatory Sequence(s) in Expression Constructs

| Constructs | Coding Sequence | Promoter | Terminator |
|---|---|---|---|
| (a) | A. terreus CAD | pTEF | XPR2t |
| (b) | A. terreus CAD | pTEF | XPR2t |
|  | E. coli CS | pRPS7 | LIP2t |
| (c) | A. terreus CAD | pTEF | XPR2t |
|  | E. coli Aco | pRPS7 | LIP2t |
| (d) | A. terreus CAD | pTEF | XPR2t |
|  | E. coli CS | pRPS7 | LIP2t |
|  | E. coli Aco | pG3P | LIP2t |

The DNA constructs described above were introduced into Yarrowia lipolytica cells by conventional methods. Positive transformants were selected on a Leucine-deficient plant and expression of the target enzymes was determined by enzymatic activity analysis.

Example 2

Production of Itaconic Acid in Genetically Modified Yarrowia Lipolytica Cells

Y. lipolytica strain YL-cad01-40, which overly expresses A. terreus CAD, was cultured overnight at 28° C. in a YPD medium containing 10 g/L yeast extract, 10 g/L peptone, and 50 mM citrate buffer, pH 4.0) and 10 g/L glucose. The overnight culture was inoculated (1%) into a rich YPD medium containing 10 g/L yeast extract, 10 g/L peptone, and 100 g/L glucose, cultured at 28° C. for 168 hours. The culture medium was collected afterwards and the amount of itaconic acid (IA) therein was determined by chromatography. The result shows that the IA concentration in the medium is about 1.05 g/L.

The same Y. lipolytica was cultured in 50 ml of the YPD medium described above until the optical density at wavelength 600 nm ($OD_{600}$) of the culture medium reached 100. Y. lipolytica cells were harvested, washed twice with ice-cold sterilized water, and then inoculated into a nitrogen-limited medium YPG (containing 100 g/L glycerol, 0.268 g/L yeast extract, and 50 mM citrate buffer, pH 4.0). The cells were cultured at 28° C. for 168 hours and the culture medium was collected afterwards. The IA concentration in the medium was found to be about 2.65 g/L.

Figure 3:
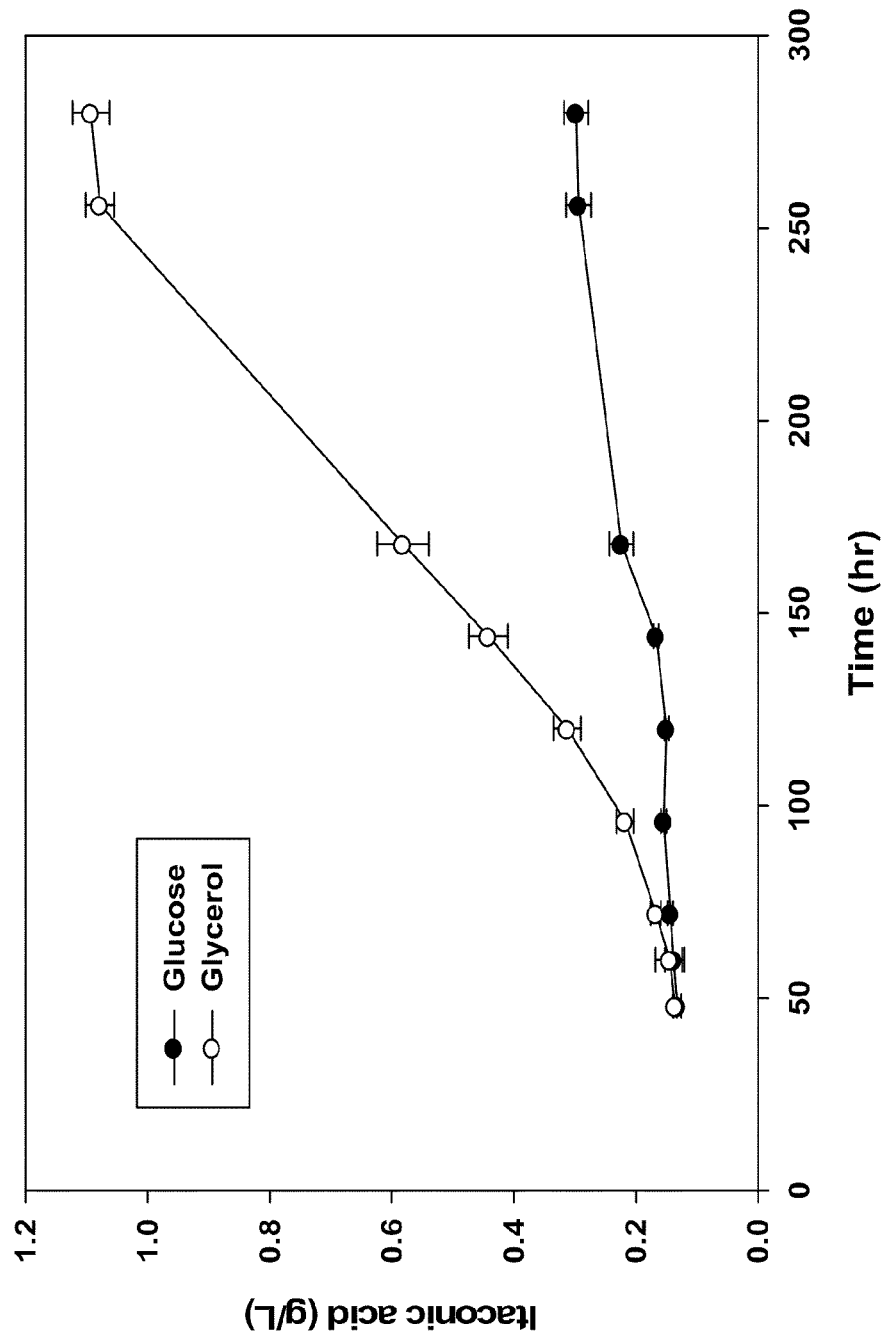
FIG. 3 is a chart showing IA concentrations in culture media containing glycerol and glucose at different time points.

IA yields using glucose or glycerol as the substrate were compared as follows. YL-cad01-40 cells were grown in the rich YPD medium until the $OD_{600}$ value of the culture reaches 150. Cells were collected via centrifugation, washed twice with ice-cold sterilized water, and then inoculated into a nitrogen-limited YPD medium (containing 0.268 g/L yeast extract and 50 mM citrate buffer, pH 4.0) supplemented with 100 g/L glycerol or 100 g/L glucose to reach an $OD_{600}$ of 150. The cells were cultured at 28° C. and culture media were collected at various time points (i.e., 48 hr, 60 hr, 72 hr, 96 hr, 120 hr, 144 hr, 168 hr, 264 hr, and 288 hr), their IA concentrations determined. As shown in FIG. 3, the IA concentrations in the medium containing glycerol were much higher than those in the medium containing glucose, indicating that using glycerol as the substrate resulted in high yields of IA in yeast cells.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of producing itaconic acid in yeast, comprising
providing a genetically modified yeast host cell, the host cell containing a first expression cassette including a first yeast promoter operably linked to a first nucleotide sequence encoding a cis-aconitic acid decarboxylase and a leader sequence upstream to the first nucleotide sequence,
culturing the yeast host cell in a medium containing glycerol at a concentration of 5-700 g/L, wherein the yeast host cell converts glycerol to itaconic acid, and
collecting the medium for isolation of itaconic acid, wherein the leader sequence encodes the amino acid sequence of MSAILSTTSKSFLSRGSTRQCQNM-QKALFALLNARHYS (SEQ ID NO:1) or MKLATAFTILTAVLA (SEQ ID NO:2), and wherein the yeast host cell is a *Yarrowia lipolytica* cell.

2. The method of claim 1, wherein the genetically modified yeast host cell further contains a second expression cassette including a second yeast promoter operably linked to a second nucleotide sequence encoding an aconitase or a citrate synthase.

3. The method of claim 1, wherein the glycerol is the sole substrate for producing itaconic acid.

4. The method of claim 3, wherein the medium contains glycerol at a concentration of 5-250 g/L.

5. The method of claim 1, wherein the first yeast promoter is selected from the group consisting of hp4d, translation elongation factor 1-α promoter (pTEF), ribosomal protein S7 prompter (pRPS7), and glycerol-3-phosphate dehydrogenase promoter (pG3P).

6. The method of claim 1, wherein the genetically modified yeast host cell further contains a second expression cassette including a second yeast promoter operably linked to a second nucleotide sequence encoding a citrate synthase, and a third expression cassette including a third yeast promoter operably linked to a third nucleotide sequence encoding an aconitase.

7. The method of claim 6, wherein the first yeast promoter is pTEF, the second promoter is pRPS7, and the third yeast promoter is pG3P.

* * * * *